US009839702B2

(12) United States Patent
Morelle et al.

(10) Patent No.: US 9,839,702 B2
(45) Date of Patent: Dec. 12, 2017

(54) METHOD FOR PURIFICATION OF 18F-LABELED CHOLINE ANALOGUES

(71) Applicant: Trasis S.A., Liege (BE)

(72) Inventors: Jean-Luc Morelle, Liege (BE); Muhammad Otabashi, Liege (BE); Gauthier Philippart, Hannut (BE); Samuel Voccia, Liege (BE)

(73) Assignee: Trasis S.A., Liege (BE)

( * ) Notice: Subject to any disclaimer, the term of this patent is extended or adjusted under 35 U.S.C. 154(b) by 0 days.

(21) Appl. No.: 14/895,842

(22) PCT Filed: Jun. 2, 2014

(86) PCT No.: PCT/EP2014/061319
§ 371 (c)(1),
(2) Date: Dec. 3, 2015

(87) PCT Pub. No.: WO2014/195249
PCT Pub. Date: Dec. 11, 2014

(65) Prior Publication Data
US 2016/0129139 A1  May 12, 2016

Related U.S. Application Data

(60) Provisional application No. 61/830,848, filed on Jun. 4, 2013.

(30) Foreign Application Priority Data

Sep. 9, 2013  (EP) .................................. 13183543

(51) Int. Cl.
C07C 213/10 (2006.01)
A61K 51/04 (2006.01)
C07B 59/00 (2006.01)

(52) U.S. Cl.
CPC .......... *A61K 51/0406* (2013.01); *A61K 51/04* (2013.01); *C07B 59/00* (2013.01); *C07B 59/001* (2013.01); *C07C 213/10* (2013.01)

(58) Field of Classification Search
None
See application file for complete search history.

(56) References Cited

FOREIGN PATENT DOCUMENTS

WO    WO 01/19484 A1     3/2001
WO    WO 2005/009928 A2  2/2005
WO    WO 2006/133732 A1  12/2006

OTHER PUBLICATIONS

Kryza, David et al. Fully automated [$^{18}$F]fluorocholine synthesis in the TracerLab MX $_{FDG}$ Coincidence synthesizer, Nuclear Medicine and Biology, 2008, pp. 255-260, vol. 35, ScienceDirect.

(Continued)

*Primary Examiner* — Sudhakar Katakam
*Assistant Examiner* — Jennifer C Sawyer
(74) *Attorney, Agent, or Firm* — Reinhart Boerner Van Deuren P.C.

(57) ABSTRACT

The present invention relates to a method for purification of 18F-labeled choline analogs in a solution injectable to a patient, prepared using non-gaseous synthesis paths, comprising a step of solid phase extraction (SPE) purification using a solid support, wherein the solid support used in the solid phase extraction purification has the characteristic to retain impurities and reagents from the solution but not the 18F-labeled choline analogs.

8 Claims, 1 Drawing Sheet

(56) References Cited

OTHER PUBLICATIONS

DeGrado, Timothy R. et al., Synthesis and Evaluation of $^{18}$F-Labeled Choline Analogs as Oncologic PET Tracers, Dec. 2001, pp. 1805-1814, vol. 42, No. 12, The Journal of Nuclear Medicine.

Pascali, Giancarlo et al., Dose-on demand of diverse $^{18}$F-fluorocholine dervatives through a two-step microfluidic approach, Nuclear Medicine and Biology, 2011, pp. 637-644, vol. 38, ScienceDirect.

Rodnick, Melissa E. et al., A fully-automated one-pot synthesis of [$^{18}$F]fluoromethylcholine with reduced dimethylaminoethanol contamination via [$^{18}$F]fluoromethyl tosylte, Applied Radiation and Isotopes, 2013, pp. 26-32, vol. 78, SciVerse ScienceDirect.

Zeisel, Steven H. et al., Choline and Human Nutrition, Annu. Rev. Nutr. 1994, pp. 269-296, Annual Reviews Inc.

Waters, the Science of What's Possible, Sep-Pak Silica Plus Light Cartridge, 120 mg Sorbent per Cartridge, 55-105 μm Particle Size, 50/pk, internet printout; 1 page; date last visited Mar. 2, 2015, http://www.waters.com/waters/partDetail.htm?partNumber=WAT023537.

Hara, Toshihiko et al., Use of $^{18}$F-choline and $^{11}$C-choline as contrast agents in positron emission tomography imaging-guided stereotactic biopsy sampling of gliomas, J Neurosurg, 2003, pp. 474-479, vol. 99.

DeGrado, Timothy R. et al., Synthesis and Evaluation of $^{18}$F-labeled Choline as an Oncologic Tracer for Positron Emission Tomography: Initial Findings in Prostate Cancer, downloaded from cacerres.aacrjournals.org, 2000, pp. 110-117, American Association for Cancer Research.

Beyerlein, Friederike et al., Automated synthesis and purification of [$^{18}$F]fluoro-[di-deutero] methyl tosylate, Journal of Labelled Compounds and Radiopharmaceuticals, 2013, pp. 360-363, vol. 56, John Wiley & Sons, Ltd.

Smith, Graham et al., Radiosynthesis and pre-clinical evaluation of [$^{18}$F]fluoro-[1, 2-$^{2}$H$_{4}$]choline, Nuclear Medicine and Biology, 2011, pp. 39-51, vol. 38, ScienceDirect.

Podo, Franca et al., Tumour Phospholipid Metabolism, Proc. Intl. Soc. Mag. Reson. Med., 2011, pp. 1-10, vol. 19.

Iwata, Ren et al., [$^{18}$F]Fluoromethyl triflate, a novel and reactive [$^{18}$F]fluoromethylating agent: preparation and application to the on-column preparation of [$^{18}$F]fluorocholine, Applied Radiation and Isotopes, 2002, pp. 347-352, Elsevier Science Ltd., vol. 57.

Hara, Toshihiko, $^{11}$C-Choline and 2-Deoxy-2-[$^{18}$F]Fluoro-D-Glucose in Tumor Imaging with Positron Emission Tomography, Molecular Imaging and Biology, 2002, pp. 267-273, vol. 4, No. 4, Elsevier Science Inc., USA.

Podo, F., Tumour Phospholipid Metabolism, NMR in Biomedicine, 1999, vol. 12, pp. 413-439.

BIO-RAD, Safety Data Sheet according to 1907/2006/EC, Article 31, printing date Jun. 17, 2015, 6 pages, Life Science Group, Environmental Health and Safety, Hercules, California.

BIO-RAD, AG 4-x4 Resin #1433341, website last visited as early as filing date of the application; www.bio-rad.com/en-cn/sku/1433341-ag-4-x4-resin, 2015.

METHOD FOR PURIFICATION OF 18F-LABELED CHOLINE ANALOGUES

FIELD OF THE INVENTION

The present invention relates to a simplified method for the purification of 18F-labeled choline analogues. This simplification allows easier automation of such radiotracer syntheses.

BACKGROUND ART

Positron Emission Tomography

Positron emission tomography (PET) is an imaging method for obtaining quantitative molecular and biochemical information of physiological processes in the body. The most common PET radiopharmaceutical in use today is [18F]-fluorodeoxyglucose ([18F]-FDG), a radiolabeled glucose molecule. PET imaging with [18F]-FDG allows to visualize glucose metabolism and has a broad range of clinical indications. Among positron emitters, 18F is the most widely used today in the clinical environment. Due to the increasing regulatory pressure, the radiopharmaceuticals are usually prepared today on single use components assembled in ready-to-use cassettes.

18F-Labeled Choline Analogues (Data Extracted from MICAD Database)

Choline is an important component of phospholipids in the cell membranes. Tissues with increased metabolism will lead to an increased uptake of choline. Choline is phosphorylated by choline kinases (CHK) to phosphorylcholine within cells, and, after several biosynthetic processes, finally is integrated into phospholipids (Zeisel S. H., Blusztajn J. K. *Choline and human nutrition*. Annu Rev Nutr. 1994; 14:269-96.). Because tumor cells have a high metabolic rate, choline uptake is high in order to keep up with the demands with the synthesis of phospholipids in their cellular membranes (Podo F. *Tumour phospholipid metabolism*. NMR Biomed. 1999; 12 (7):413-39.).

Positron emission tomography (PET) with [11C]choline has been reported to be useful for the detection and differential diagnosis of brain tumors, prostate cancer, lung cancer, and esophageal cancer (Hara T. [11C]-*choline and 2-deoxy-2-[18F]fluoro-D-glucose in tumor imaging with positron emission tomography*. Mol Imaging Biol. 2002; 4 (4):267-73.). However, [11C]choline has a high uptake in liver, kidney, and spleen. [18F]-labeled choline analog was initially synthesized as [18F]fluoroethylcholine to replace [11C]choline as a PET tracer due to the short physical half-life of 11C (Hara T., Yuasa M. *Automated synthesis of fluorine-18 labeled choline analogue: 2-fluoroetheyl-dimethyl-2-oxyethylammonium*. J Nucl Med. 1997; 38 Supplement:44P.). Although 18F has a longer half-life (110 min), [18F]fluoroethylcholine showed a rapid accumulation in the urinary bladder, rendering it less desirable for imaging prostate cancer and pelvic lymph nodes. Therefore, [18F] fluorocholine (FCH) was conceived to be a better biological analog than [18F]fluoroethylcholine (DeGrado T. R., Coleman R. E., Wang S., Baldwin S. W., Orr M. D., Robertson C. N., Polascik T. J., Price D. T. *Synthesis and evaluation of 18F-labeled choline as an oncologic tracer for positron emission tomography: initial findings in prostate cancer*. Cancer Res. 2001; 61 (1):110-7.). FCH PET studies showed high uptake in malignancies in patients with prostate cancer, breast carcinoma, and brain tumors (DeGrado T. R., Baldwin S. W., Wang S., Orr M. D., Liao R. P., Friedman H. S., Reiman R., Price D. T., Coleman R. E. *Synthesis and evaluation of (18)F-labeled choline analogs as oncologic PET tracers*. J Nucl Med. 2001; 42 (12):1805-14; Hara T., Kondo T., Hara T., Kosaka N. *Use of 18F-choline and 11C-choline as contrast agents in positron emission tomography imaging-guided stereotactic biopsy sampling of gliomas*. J Neurosurg. 2003; 99 (3):474-9.).

Synthesis Methods

Standard Method Involving Gaseous Intermediates

[18F]Choline is generally synthesized from [18F]fluorobromomethane and dimethylethanolamine (DMEA) with a radiochemical purity greater than 98% and a radiochemical yield (not corrected for decay) for the synthesis and purification was approximately 20-40%. (DeGrado T. R., Coleman R. E., Wang S., Baldwin S. W., Orr M. D., Robertson C. N., Polascik T. J., Price D. T. *Synthesis and evaluation of 18F-labeled choline as an oncologic tracer for positron emission tomography: initial findings in prostate cancer*. Cancer Res. 2001; 61 (1):110-7.) In D. Kryza et al (*Fully automated [18F]fluorocholine synthesis in the TracerLab MXFDG Coincidence synthesizer*. Nucl. Med. Biol. 35 (2), 2008: 255-260), [18F]Fluorocholine was prepared by N-alkylation of DMAE with [18F]fluorobromomethane ($BrCH_2F$), followed by purification on a CM cartridge.

Another automated method of FCH synthesis was achieved through the formation of [18F]fluoromethyl triflate and the reaction of [18F]fluoromethyl triflate with DMEA on a Sep-Pak column. The total time required for obtaining the finished chemical was 30 min. The radiochemical yield (decay corrected) was 80% with the radiochemical purity and chemical purity of >98%. (Iwata R., Pascali C., Bogni A., Furumoto S., Terasaki K., Yanai K. [*18F*]*fluoromethyl triflate, a novel and reactive [18F]fluoromethylating agent: preparation and application to the on-column preparation of [18F]fluorocholine*. Appl Radiat Isot. 2002; 57 (3):347-52.)

Alternative Methods Using Ditosylates as Precursor

G. Smith et al (Nucl Med Biol. 2011 January; 38 (1):39-51) have compared the synthesis of [18F]fluorocholine, by the alkylation of the relevant precursor, i.e. DMEA, with [18F]fluorobromomethane or [18F]fluoromethyl tosylate. Alkylation with [18F]fluoromethyl tosylate proved to be the most reliable radiosynthetic route.

In WO 2005/009928, J. Lim has shown the preparation of [18F] FCH in a 2-steps reaction: fluorination of ditosylmethane with [18F] fluoride followed by an alkylation reaction with [18F]fluoromethane tosylate and dimethylethanolamine using a [18F]FCH was purified using a Silica Sep-Pak column (Catalog No. WAT023537, Waters Corporation, Milford, Mass.). The column was washed with ethanol and water to remove all impurities and [18F] FCH was eluted with 2% acetic acid. The acetic acid was removed using an AG 4-X4 weakly basic ion-exchange resin column (143-3341, Bio-Rad Laboratories, Inc., Hercules, Calif.).

It was shown by G. Pascali et al (*Dose-on-demand of diverse 18F-fluorocholine derivatives through a two-step microfluidic approach*. Nucl. Med. Biol. 38 (5), 2011: 637-644) that the radiolabeling step results in the formation of two [18F]-labeled species among which [18F]fluoromethane tosylate. Despite this method uses non-gaseous intermediates, no purification method is carried out or proposed in order to eliminate impurities and side products resulting from this reaction path. Beyerlein et al have evidenced that the second compound is [18F]-labeled Tosyl Fluoride (Beyerlein et al, J. Label Compd. Radiopharm. Vol 56 (14), 2013).

It was recently demonstrated (Rodnick et al, Applied Radiation and Isotopes 78 (2013)26-32) the presence of cold impurities generated during the quaternization reaction, e.g.

the reaction of methane ditosylate with DMAE, especially when doing one-pot labeling and quaternization, these impurities being present in the final product. These impurities have to be eliminated and up to recently, the only method to perform a reliable purification was high pressure liquid chromatography.

Problem to be Solved

[18F]choline has been shown to be the best 18F-labeled choline analogue. However, the most widely used synthesis path for this tracer involves a gas chromatography step, i.e. the handling of a radioactive gaseous compound. This gas chromatography step is very tedious to implement, especially on single use cassette-based system, and possible leaks make the production of this radiopharmaceutical critical. Alternative synthesis methods are thus highly desirable.

Among the alternatives, the use of non-gaseous synthesis path using non-gazeous quaternization agents has been proposed, e.g. use of [18F]-fluoromethyltosylate, but these alternative paths still request an HPLC purification of the final product due to the presence in the bulk product of non-desirable impurities. Due to the short lifetime of radioisotopes, the purification method is a key aspect in radiopharmaceutical production. Thus, if long and non-disposable HPLC purification steps can be avoided, it is a huge benefit. The method of choice must also be effective enough and reliable to ensure a high level of radiochemical purity.

Aim of the Invention

The present invention aims at making the non-gaseous paths for the synthesis of 18F-labeled choline analogues, i.e. the methane ditosylate path, easy automate by allowing a one-pot synthesis to be performed while avoiding the necessity of the HPLC purification of the crude 18F-labeled choline analogue.

DISCLOSURE OF THE INVENTION

Figure 1:
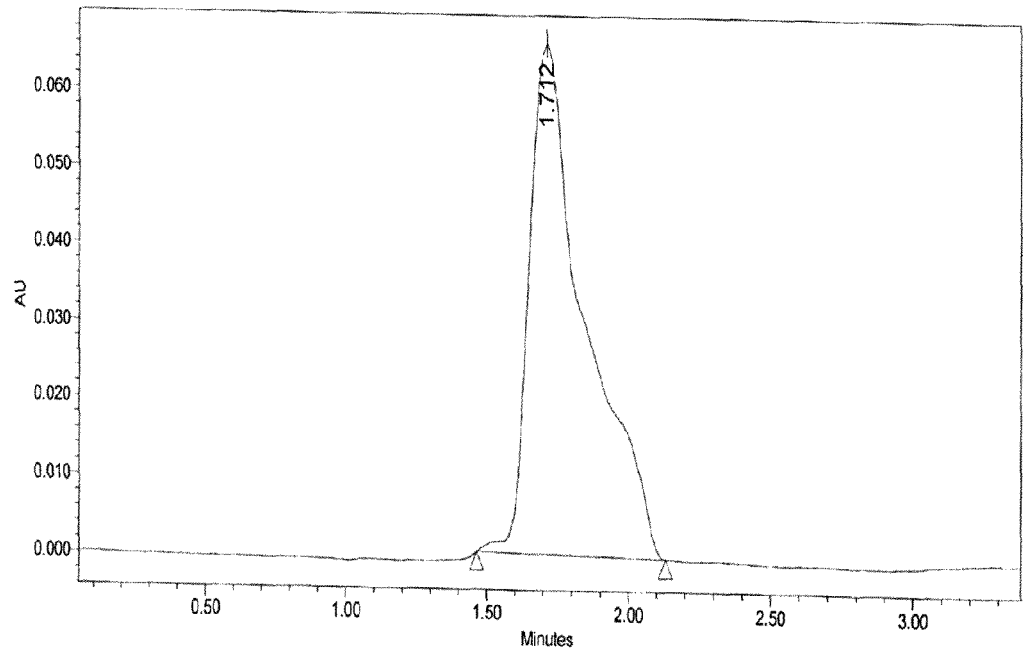
FIG. 1 represents an impurity chromatogram for a synthesis example of [18F]FCH before SPE purification.

The method of the present invention allows the purification of 18F-labeled choline analogues, prepared using non-gaseous synthesis paths (by opposition to the path involving gas chromatography step with [18F]bromofluoromethane) by the use of a reliable solid phase extraction (SPE) purification step of the final synthesis bulk product. Moreover, the resulting tracer solution is readily injectable to a patient. It brings two advantages: the reduction of the preparation duration, which results in an increase of the overall yield, and a simplification of the automated equipment needed for the synthesis of a radiopharmaceutical. In particular, the suppression of any HPLC purification step facilitates the automation of the synthesis. The non-gaseous synthesis paths may involve alkylating agents with a leaving group such as tosylate, mesylate and triflate.

According to the present invention, the purification process is performed by passing the bulk of the synthesis of the 18F-labeled choline analogues on a non-ionic solid support. This solid support has the characteristic to retain the quaternization products and non-polar products (such as the precursor) but not the 18F-labeled choline analogues in an aqueous solution.

According to the present invention, the purification process of the method is performed by passing the [18F]-labeled choline analogues solution through a solid phase extraction column containing a solid support. The impurities are trapped on the modified solid support while 18F-labeled choline analogues are not retained.

In some embodiments of the present invention, the solid support is selected from the group of solid phase extraction resins and liquid chromatography resins consisting of polar and non-polar phases functionalized with or made of alkyl chains comprising 1 to 30 carbon atoms, polystyrene, poly (divinylbenzene), poly(styrene-divinylbenzene), phenyl, polyamide, amino propyl (NH2), cyanopropyl (CN), alcohols or diols, carboxymethyl, hydroxylated poly(styrene-divinylbenzene), diethylaminoethyl, quaternary aminoethyl, sulfopropyl, etc.

In some preferred embodiments of the invention, the solid support is selected from the group consisting of solid phase extraction resins and liquid chromatography resins having intermediate polar/non-polar and/or hydrophilic/lipophilic properties. These properties generally result from the copolymerization of divinylbenzene and/or styrene, or the surface functionalization of preformed beads made of (co) polymers of divinylbenzene and styrene by the copolymerization with a co-monomer (vinyl compound). Suitable vinyl compounds used for copolymerization or surface functionalization include vinylpyrrolidone, vinylacetate, (methacryloyloxymethyl)naphtalene, 4,4'-bis(maleimido)diphenylmethane, p,p'-dihydroxydiphenylmethane diglycidylmethacrylic ester, p,p'-dihydroxydiphenylpropane diglycidyl methacrylic ester, 2-hydroxyethyl methacrylate (HEMA), 2,2-dimethylaminoethyl methacrylate (DMAEMA), ethylenedimethacrylate glycidylmethacrylate, N-vinylcarbazole, acrylonitrile, vinylpyridine, N-methyl-N-vinylacetamide, aminostyrene, methylacrylate, ethylacrylate, methylmethacrylate, N-vinylcaprolactam, N-methyl-N-vinylacetamide. Brand names for these solid supports are Oasis® HLB from Waters, H2O-Philic DVB from Mallinckrodt™ J. T. Baker®, Waters Porapak™ RDX, Strata-X™ and Synergi™ Polar-RP from Phenomenex®, etc.

In some embodiments of the present invention, the solid support is selected from the group of solid phase extraction resins and liquid chromatography resins having intermediate polar/non-polar and/or hydrophilic/lipophilic properties such as graphitized carbon phase. Brand names for these solid supports are Hypercarb™ from Thermo Electron Corp. and Carbograph from Alltech.

EXAMPLE

This example shows how the bulk product from a [18F] FCH synthesis with the synthesis path below can be cleaned up using Phenomenex® Strata-X™ cartridges, containing a reversed phase functionalized polymeric sorbent that gives strong retention of neutral, acidic, or basic compounds under aggressive, high organic wash conditions. This sorbent relies on 3 mechanisms of retention: pi-pi bonding, hydrogen bonding (dipole-dipole interactions), and hydrophobic interaction.

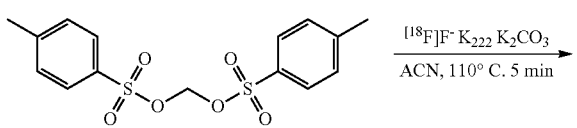

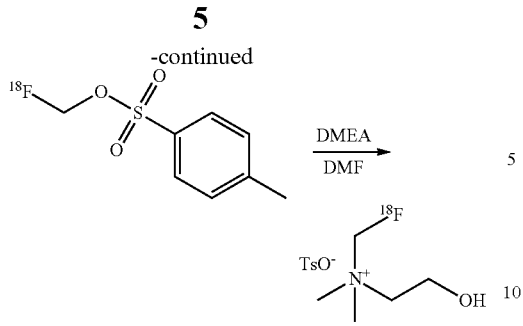

[18F]FCH was prepared in two main chemical steps from the starting material methylene bis(toluene-4-sulfonate). This reagent reacts with [18F]fluoride to give [18F]fluoromethylene toluene-4-sulfonate. This compound is allowed to react with dimethylaminoethanol (DMAE) to afford [18F]FCH. The crude solution is purified on a cation exchange cartridge on which the [18F]FCH is trapped. The [18F]FCH is then eluted from the cartridge and passed through the purification cartridges directly to the bulk product vial.

Figure 2:
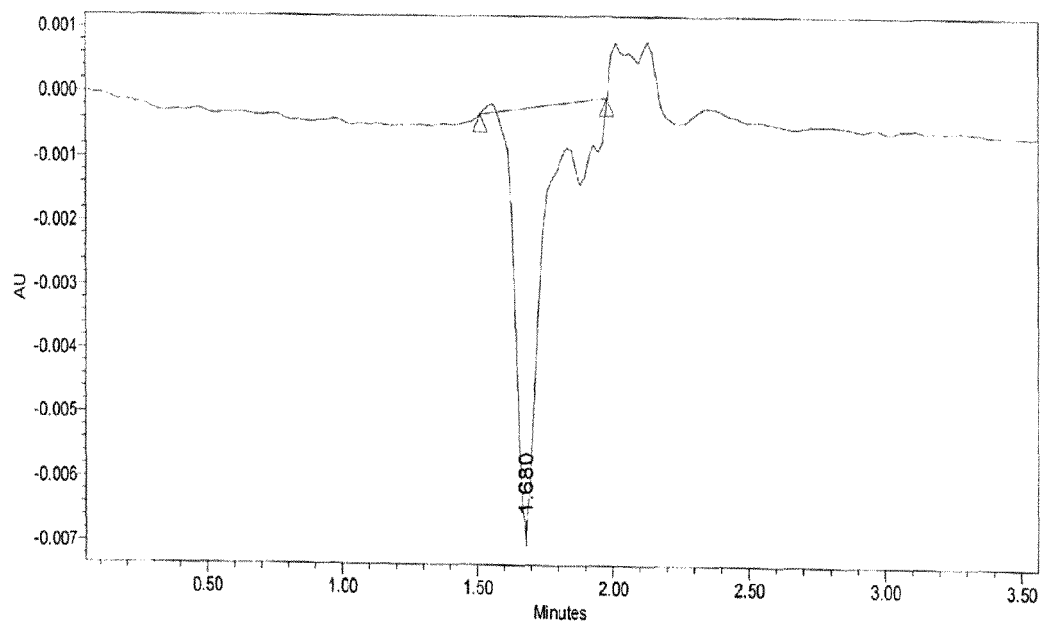
FIG. 2 represents the impurity chromatogram for the same synthesis example of [18F]FCH after SPE purification.

[18F]FCH obtained from the preparation path above shows the presence of an impurity which is a quaternization product resulting from the reaction between DMAE and methylene bis(toluene-4-sulfonate). The chromatograms obtained before and after SPE (Phenomenex® Strata-X™) purification are given in FIGS. 1 and 2 respectively. This demonstrate the ability of the purification method described in this patent to eliminate these quaternized impurities.

The invention claimed is:

1. A purification method of a 18F-labeled fluorinated choline analogue in a solution injectable to a patient, prepared using non-gaseous synthesis paths, sequentially comprising:
    a starting step from a synthesis bulk product or synthesis crude solution;
    a first purification step of the synthesis bulk product on a cation exchange cartridge for trapping the 18F-labeled fluorinated choline analogue;
    an elution of trapped 18F-labeled fluorinated choline analogue from said cation exchange cartridge;
    a second purification step of the eluted 18F-labeled fluorinated choline analogue solution by solid phase extraction (SPE) using a non-ionic solid support, for retaining impurities and reagents from the eluted solution but not the 18F-labeled fluorinated choline analogue, wherein said impurities and reagents are essentially aromatic quaternization products and non-polar products,
    wherein the non-ionic solid support is selected from the group consisting of solid phase extraction resins and liquid chromatography resins comprising a copolymer of divinylbenzene and/or styrene with a comonomer vinyl compound, or
    wherein the solid support is selected from the group of solid phase extraction resins and liquid chromatography resins comprising a graphitized carbon phase.

2. The method of claim 1, wherein the non-gaseous synthesis paths involve alkylating agents with a leaving group selected from the group consisting of tosylate, mesylate and triflate.

3. The method of claim 1, wherein the vinyl compounds used for copolymerization is selected from the group consisting of vinylpyrrolidone, vinylacetate, (methacryloyloxymethyl)naphtalene, 4,4'-bis(maleimido)diphenylmethane, p,p'-dihydroxydiphenylmethane diglycidylmethacrylic ester, p,p'-dihydroxydiphenylpropane diglycidyl methacrylic ester, 2-hydroxyethyl methacrylate (HEMA), 2,2-dimethylaminoethyl methacrylate (DMAEMA), ethylenedimethacrylate glycidylmethacrylate, N-vinylcarbazole, acrylonitrile, vinylpyridine, N-methyl-N-vinylacetamide, aminostyrene, methylacrylate, ethylacrylate, methylmethacrylate, N-vinylcaprolactam, and N-methyl-N-vinylacetamide.

4. The method of claim 1, wherein the solid support is obtained by surface functionalization of preformed beads made of (co)polymers of divinylbenzene and/or styrene by the copolymerization with a co-monomer vinyl compound.

5. The method of claim 3, wherein the vinyl compound used for copolymerization is vinylpyrrolidone.

6. The method of claim 2, wherein the alkylating agent having a leaving group is selected to be a tosylate alkylating agent.

7. The method of claim 6, wherein the impurity under the form of an aromatic quaternization product results from the reaction between demethylaminoethanol (DMEA) with the precursor methylene bis(toluene-4-sulfonate).

8. The method of claim 6, wherein the alkylating agent having a leaving group is methylene bis(toluene-4-sulfonate).

* * * * *